(12) United States Patent
Chu et al.

(10) Patent No.: US 7,977,820 B2
(45) Date of Patent: Jul. 12, 2011

(54) ULTRASOUND TRANSMIT PULSE GENERATOR

(75) Inventors: Ching Chu, San Jose, CA (US); Benedict C. K. Choy, Cupertino, CA (US)

(73) Assignee: Supertex, Inc., Sunnyvale, CA (US)

( * ) Notice: Subject to any disclaimer, the term of this patent is extended or adjusted under 35 U.S.C. 154(b) by 392 days.

(21) Appl. No.: 12/354,137

(22) Filed: Jan. 15, 2009

(65) Prior Publication Data

US 2009/0206676 A1 Aug. 20, 2009

Related U.S. Application Data

(60) Provisional application No. 61/028,736, filed on Feb. 14, 2008.

(51) Int. Cl.
*H03K 3/00* (2006.01)

(52) U.S. Cl. ...................................................... 307/106
(58) Field of Classification Search .................. 307/106, 307/421; 327/99, 106, 114, 164, 165, 184, 327/291, 10
See application file for complete search history.

(56) References Cited

U.S. PATENT DOCUMENTS

| | | | | |
|---|---|---|---|---|
| 7,075,474 B2* | 7/2006 | Yamagata et al. | ............ | 341/169 |
| 7,312,657 B2* | 12/2007 | Kurokawa | ............ | 330/251 |
| 7,357,471 B2* | 4/2008 | Clark | ............ | 347/9 |
| 7,504,866 B2* | 3/2009 | Lee | ............ | 327/78 |

* cited by examiner

*Primary Examiner* — Albert W Paladini
(74) *Attorney, Agent, or Firm* — Jeffrey D. Moy; Weiss & Moy, P.C.

(57) ABSTRACT

A ultrasound transmit pulse waveform generator for driving a piezoelectric transducer in medical ultrasound imaging, non-destructive testing (NDT) ultrasound imaging applications, includes a capacitor, switching programmable current sources, and a power amplifier.

30 Claims, 4 Drawing Sheets

ULTRASOUND TRANSMIT PULSE GENERATOR

RELATED APPLICATIONS

This patent application claims the benefit of U.S. Provisional Application No. 61/028,736, filed Feb. 14, 2008, entitled "ULTRASOUND TRANSMIT PULSE GENERATOR," in the name of the same inventors, and which is incorporated herein by reference in its entirety.

TECHNICAL FIELD

This invention relates to an ultrasound transmit pulse waveform generator, and more particularly, to an ultrasound transmit pulse waveform generator for driving a piezoelectric transducer array probe.

BACKGROUND

Ultrasound array transmitters in medical or nondestructive testing (NDT) imaging application have a growing demand for more sophisticated electrical excitation waveforms to generate well-focused, high resolution targeted, coherently formed, high frequency acoustic dynamic scanning beams. The conventional ultrasound transmit pulse generator circuits that can generate two different voltage amplitudes of bidirectional and return-to-zero pulses (such as a 5-level pulser) include at least six high-voltage high current MOSFET transistors in an output stage, such as described below in conjunction with FIG. 1. The cost per transmit channel of such pursers compared to a 2-level or 3-level pulser increases dramatically.

Therefore, a need exists to provide a device and method to overcome the above problem.

SUMMARY

The circuit configurations, principles, methods and topology are disclosed here will be used for the integrated digital programmable high-voltage waveform generators circuits implementation of the multi-channel, advanced, cost-effective for the ultrasound array-transducer excitation transmit waveform generators in medical ultrasound imaging and NDT ultrasound inspection instrumentation.

The waveform generators described herein provide digital controlled, programmable high voltage waveform multiple generator channels that may be integrated into very small integrated circuits (ICs) with low cost.

DETAILED DESCRIPTION

In various embodiments, the waveform generators of the present invention provide ultrasound imaging probe transducer excitation using a large number array of high voltage and high current transmit pulse waveform generators that may be controlled by a digital logic interface directly with fast response and precise timing. Electronics controlled dynamic focus, acoustic phase-array, and transmitting beamforming technology may be used in color Doppler image portable ultrasound machines. In various embodiments, the waveform generators of the present invention provide digital controlled, programmable high voltage waveform multiple generator channels that are integrated into very small ICs. In various embodiments, the waveform generators of the present invention may generate various transmitting waveforms, and include only two high current output stage MOSFETs.

Figure 1:
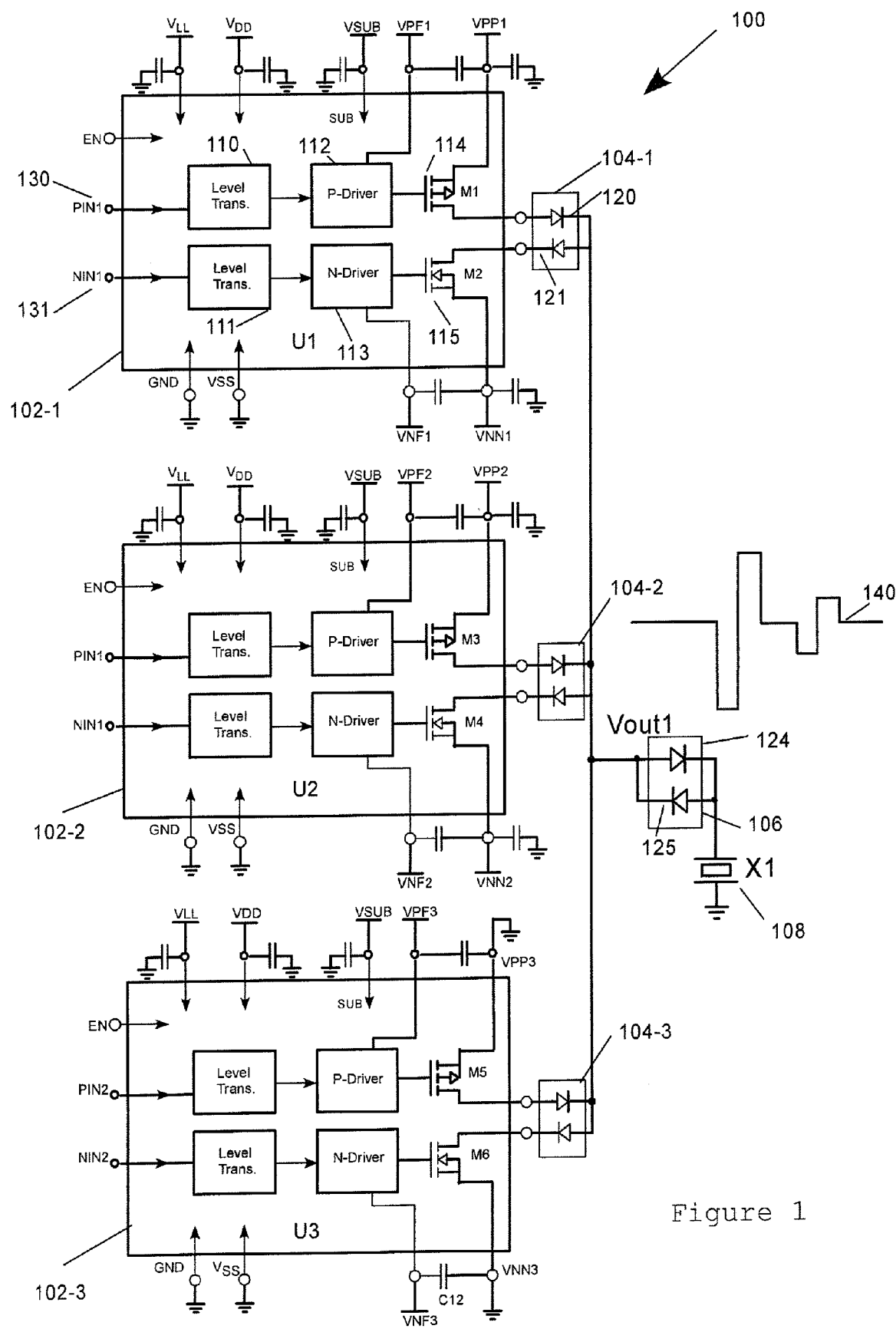
FIG. 1 is a schematic diagram illustrating a conventional 5-Level high voltage pulser with a return-to zero (RTZ) function.

FIG. 1 is a schematic diagram illustrating a conventional 5-level high voltage pulser 100 with a return-to-zero (RTZ) function. The pulser 100 generates a 5-level high voltage waveform 140. The pulser 100 comprises a plurality of power amplifiers 102-1 through 102-3, a plurality of diode protection circuits 104-1 through 104-3, a cross coupled diode circuit 106, and a transducer 108.

Each power amplifier 102-1 through 102-3 comprises a plurality of level translators 110 and 111, a P-driver 112, an N-driver 113, a PMOS transistor 114, and an NMOS transistor 115. For simplicity and clarity, reference numbers are shown only in the power amplifier 102-1. Each diode circuit 104-1 through 104-3 comprises a plurality of diodes 120 and 121. For simplicity and clarity, reference numbers are shown only in the diode circuit 104-1. The cross coupled diode circuit 106 comprises a plurality of diodes 124 and 125 arranged in a cross coupled configuration with the anode of the diode 124 coupled to the cathode of the diode 125 and the cathode of the diode 124 being coupled to the anode of the diode 125. In one embodiment, the transducer 108 may be an electroactive lens, or a piezoelectric element.

In the power amplifiers 102-1 through 102-3, the level translator 110 shifts the voltage level of an input signal 130 and provides the level shifted signal to the P-driver 112. The P-driver 112 controls the gate of the PMOS transistor 114, which is arranged in a source follower power amplifier configuration between a voltage source VPP1 and the cathode of the diode 120 of the diode protection circuit 104. The PMOS transistor 114 and the NMOS transistor 115 are driven by the directly coupled MOSFET gate drivers 112 and 113, respectively. The PMOS transistor 112 provides the amplified signal through the diode 124 of the cross coupled diode circuit 106 to the transducer 108. The level translator 111 shifts the voltage level of an input signal 131 and provides the level shifted signal to the N-driver 113. The N-driver 113 controls the gate of the NMOS transistor 114, which is arranged in a source follower power amplifier configuration between the anode of the diode 121 of the diode protection circuit 121 and a negative voltage source VNN1. The NMOS transistor 114 receives amplified signal through the diode 125 of the cross coupled diode circuit 106 from the transducer 108.

Figure 2:
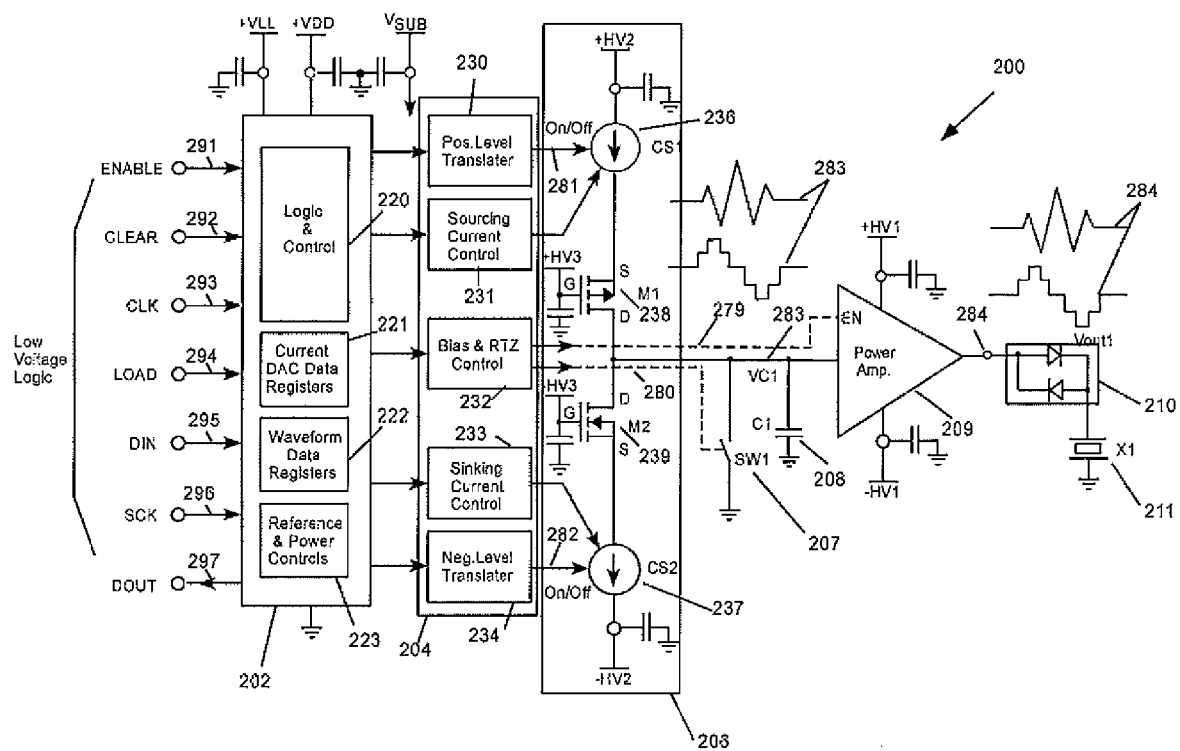
FIG. 2 is a schematic diagram illustrating a waveform generator circuit that includes a capacitor and switching current-source and power amplifier stage for ultrasound transmit excitation applications in accordance with the present invention.

FIG. 2 is a schematic diagram illustrating a waveform generator circuit 200. The circuit 200 comprises a control circuit 202, a current control circuit 204, a current source circuit 206, a switch 207, a capacitor 208, a power amplifier 209, a cross coupled diode circuit 210, and a transducer 211. The waveform generator circuit 200 may be an ultrasound transmit pulse waveform generator for driving a piezoelectric transducer array probe, for various applications, such as medical ultrasound imaging or NDT ultrasound imaging.

The control circuit 202 provides control signals to the current control circuit 204 for setting the parameters for the output currents and voltages of the current source circuit 206 for controlling the shape of the output waveform. The control circuit 202 receives a plurality of low voltage logic control signals including an enable signal 291, a clear signal 292, a clock signal 293, a load signal 294, input data 295, a serial-clock signal 296, and has a data output 297. The current control circuit 204 generates on and off signals 281 and 282, an enable signal 279 and a switch control signal 280. The control circuit 202 comprises a logic & control circuit 220, a current digital-to-analog converter (DAC) data registers 221, a waveform data register 222, and a reference & power control circuit 223. The control circuit 204 comprises a positive level translator 230, a source and current control circuit 231, a bias & RTZ control circuit 232, a sinking current control circuit 233 and a negative level translator 234.

The current source 206 comprises a plurality of current sources 236 and 237, a PMOS transistor 238, and an NMOS transistor 239. The positive level translator 230 provides an on-off control signal to the current source 236. The source and current control 231 provides a control signal for varying the current provided by the current source 236. The current source 236, the PMOS transistor 238, the NMOS transistor 239 and the current source 237 are coupled in a series between a high voltage (HV2) and the negative high voltage (−HV2). The gates of the PMOS transistor 238 and the NMOS transistor 239 are biased by a positive high voltage HV3 and a negative high voltage (−HV3), respectively. The bias & RTZ control circuit 232 provides an enable signal 279 to the power amplifier 209 and a control signal 280 to the switch 207. The amplifier 209 amplifies the output of the current source 206 and applies the amplified output to the cross coupled diode circuit 210. In one embodiment, the power amplifier 209 is a buffer. The switch 207 selectively grounds the input of the power amplifier 209 and shorts the capacitor 208 to ground in response to the switch control signal 280. The switch 207 is controlled to provide that the voltage across the capacitor 208 equals zero at some time, by operating the switch 207 as a return-to-zero switch. The capacitor 208 is coupled between the input of the power amplifier 209 and ground. In one embodiment, the transducer 211 may be a piezoelectric or electrostatic transducer, or a piezoelectric or electrostatic transducer array probe.

The transistors 238 and 239 may be arranged as a current source cascode. In one embodiment, the transistors 238 and 239 may be deletion or enhancement type, complementary N-channel and P-channel MOSFETs for sourcing and sinking current into or out of the capacitor 208. The sourcing or sinking current sources may be single or multiple channels, including sourcing or sinking to or from the high voltage supply rail or zero volt common ground. The capacitor 208 may be a built-in capacitor on the IC chip or external to the IC chip as on PCB component(s), or on/in the IC chip as hybrid circuit component(s).

The voltage across the capacitor 208 is inputted to the power amplifier 209, and the output of the power amplifier 209 drives the transducer 211. Because of the power or current amplification of the amplifier 209, the generation of a waveform 281 at the capacitor 208 is a much smaller current version of the output waveform 282 applied to the transducer 211. In other words, the generation of the input waveform 281 has a higher impedance than the output impedance of the power amplifier 209, although both may have the same or similar high voltage ranges. Therefore, the Silicon circuit of the waveform generator 200 for the input may be a much smaller size than the output MOSFET.

The voltage across the capacitor 208 is being controlled by a group of high voltage, sourcing or sinking, switching current-sources. The on or off of these current-sources are predetermined by the waveform parameters stored in the digital waveform data register 222. The timing of the on or off of the current-sources 236 and 237 is clocked by the input clock signal of the clock (CLK) 293. The amplitude of these current sources are controlled by the current DAC(s) 221, which are predetermined digital input via the serial or parallel digital DCA data interface.

Because of the high input impedance of the power amplifier 209, the proper size of the capacitor 208, and the constant or almost constant current to charge or discharge the capacitor 208, the output ultrasound waveform may have a high frequency, and thus a time period that is short. Further, the waveform 281 on the capacitor 208 may be selected to be trapezoid, triangle, piecewise-linear or almost-trapezoid, almost-triangle, or piecewise almost-linear. Because the time to charge or discharge the capacitor 208 less than the time of the digital input signal or the waveform data control, the generated waveform 281 may be considered as arbitrary or almost-arbitrary waveform(s)

In one embodiment, he slew rate of the voltage on the capacitor 208 has a range of 0.08V/ns to 200V/ns. The voltage gain of the amplifier 209 or source or emitter follower has a range of 0.5 to 2.0. The frequency range of the waveform generator 200 is 20 kHz to 200 MHz.

Figure 3:
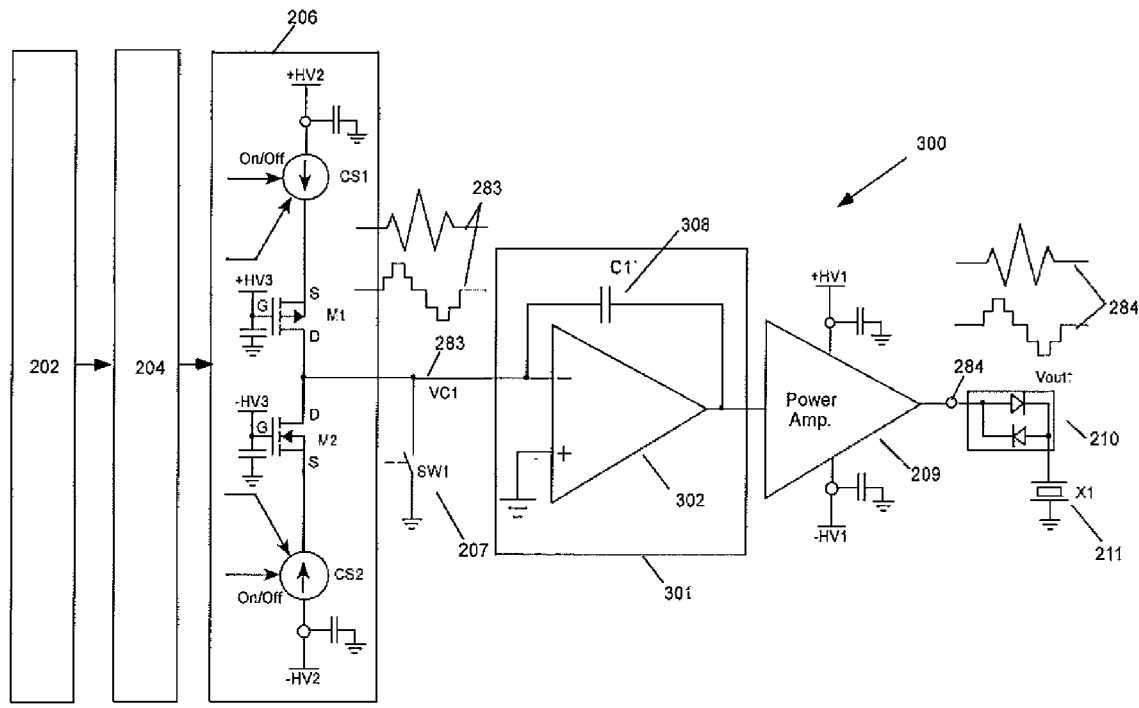
FIG. 3 is a schematic diagram illustrating a waveform generator circuit including a current integration capacitor in a virtual-ground configuration in accordance with another embodiment of the present invention.

FIG. 3 is a schematic diagram illustrating a waveform generator circuit 300. The waveform generator 300 provides a current integration capacitor in a virtual-ground configuration. The waveform generator circuit 300 comprises a control circuit 202, a current control circuit 204, a current source circuit 206, a switch 207, an operational amplifier 302, a capacitor 308, a power amplifier 209, a cross coupled diode circuit 210 and a transducer 211. For clarity and simplicity, the current control circuit 204 and the current source circuit 206 are shown only as blocks. The operational amplifier 302 and the capacitor 308 are arranged to operate as an integrator 301 of the output of the current source circuit and to provide the integrated output to the power amplifier 209.

The integration capacitor 308 is configured differently at a virtual-ground opamp feedback control circuit. This configuration may increases the linearity of the waveform curves with these applications, and also provides a non ground capacitor feature for the circuit.

In one embodiment, the current control circuit 204 reduces the power consumption of the power amplifier 209 when there is no waveform at the output or echo-waiting period for the ultrasound imaging system. The current control circuit 279 may also include a bias circuit enable signal to enable the bias current of the power amplifier 203 only for the time period of transmitting. This bias control circuitry reduces the power consumption of the waveform generators)

Figure 4:
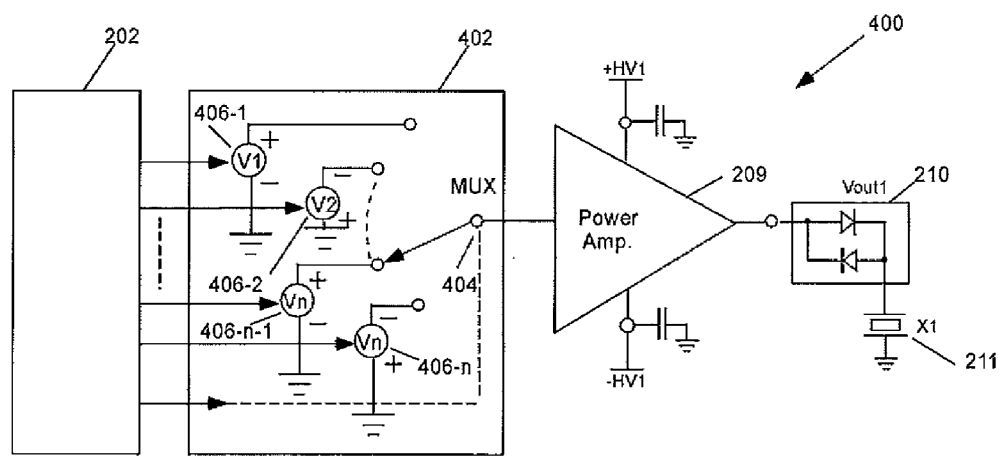
FIG. 4 is a schematic diagram illustrating a waveform generator circuit including a multiplexer and a plurality of voltage sources in accordance with yet another embodiment of the present invention.

FIG. 4 is a schematic diagram illustrating a waveform generator 400. The waveform generator 400 includes a multiplexer and voltage source configuration. The waveform generator circuit 400 comprises a selectable voltage circuit 402, a power amplifier 209, a cross-coupled diode circuit 210, and a transducer 211. The selectable voltage circuit 402 comprises a multiplexer 404 and a plurality of voltage sources 406-1 through 406-n that each provide a corresponding voltage $V_1$ through $V_n$. The multiplexer 404 selectively couples one of the voltage sources 406 to the input of the power amplifier 209. The logic signal controlled multiplexer 404 provides the control signal for this generator. The logic control 202 (see FIG. 2) may provide the control signals to the selectable voltage circuit 402 to generate a desired output waveform from the power amplifier 209.

Figure 5:
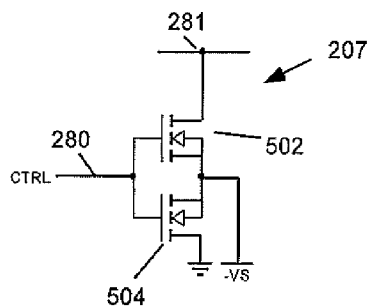
FIG. 5 is a schematic diagram illustrating a bidirectional analog switch of the waveform generator circuits of FIGS. 2, 3 and 4 and including a back-to-back MOSFET configuration.

FIG. 5 is a schematic diagram illustrating one embodiment of the switch 207. In one embodiment, the switch 207 is a bidirectional analog switch having a back-to-back MOSFET configuration. The switch 207 comprises a plurality of NMOS transistors 502 and 504 coupled in series, and enabled by a control signal 506 applied to the gates of the NMOS transistors 502 and 504. The drain of the NMOS transistor 502 is coupled to the input 281 of the power amplifier 209.

Figure 6:
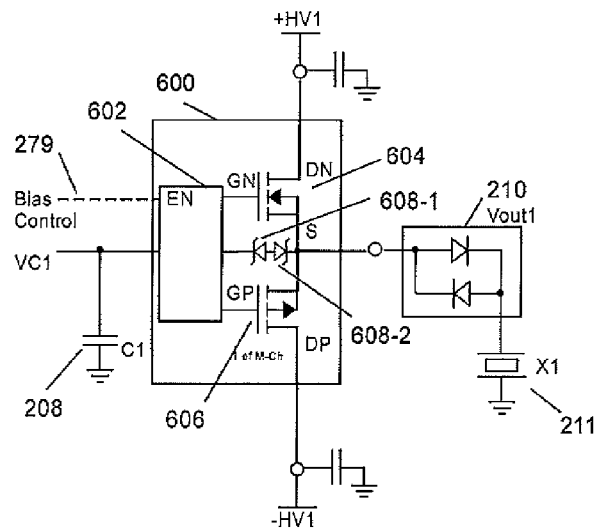
FIG. 6 is a schematic diagram illustrating one embodiment of a power amplifier of the waveform generator circuits of FIGS. 2, 3 and 4 and having a complementary MOSFET source-follower power amplifier configuration.

FIG. 6 is a schematic diagram illustrating a power amplifier 600. The power amplifier 600 may be used as the power amplifier 209 in the waveform generator circuits of FIGS. 2, 3 and 4. The power amplifier 600 has a complementary MOSFET source-follower power amplifier configuration. The power amplifier 600 comprises a driver stage 602, an NMOS transistor 604, a PMOS transistor 606, and a plurality of Zener diodes 608-1 and 608-2.

The driver stage 602 provides the gate bias to the transistors 604 and 606. The NMOS transistor 604 and the PMOS transistor 606 are coupled in series between a positive high voltage (+HV1) and a negative high voltage source (−HV1) and the node formed of the sources of the transistors 604 and 606 is coupled to an output node of the power amplifier 600.

In response to the voltage VC1, the driver stage 602 provides a voltage through the Zener diodes 608 to the transistors 604 and 606 for amplification, and application through the cross-coupled diode circuit 210 to the transducer 211. The driver stage 602 also provides gate voltages to the gates of the NMOS transistor 604 and the PMOS transistor 606 in response to a bias control signal 610 for controlling the voltage on the output node of the power amplifier 600. The bias control signal 610 may also function as an enable signal. In one embodiment, the bias & RTZ control circuit 232 (FIG. 2) provides the bias control signal 610. In an alternative embodiment, the power amplifier 600 may have a complementary bipolar transistor emitter-follower power amplifier configuration in which npn and pnp bipolar transistors replace the MOSFET transistors 604 and 606. The source follower or followers may be single or multiple channels built in the waveform generator IC package or in separate packages.

Figure 7:
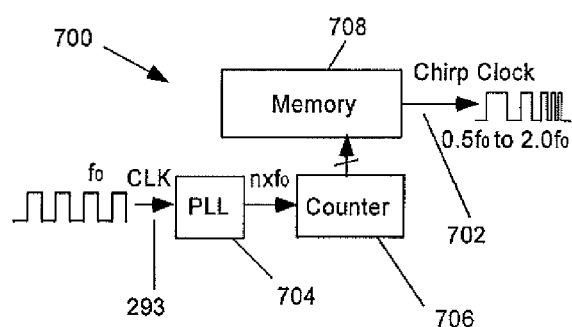
FIG. 7 is a schematic diagram illustrating a clock generator.

FIG. 7 is a schematic diagram illustrating a clock generator 700. In one embodiment, the control circuit 202 (FIG. 2) includes the clock generator 700. The clock generator 700 generates a clock 702 in response to the clock 293. In one embodiment, the chirp clock generator 700 may selectively generate a clock 702 that is a regular digital clock with evenly spaced time cycles or is a chirp clock. In one embodiment, the clock generator 700 is a chirp clock generator. In another embodiment, the clock 702 may be a frequency linearly modulated or non-linearly modulated, with predetermined timing or frequency range chirp. The clock generator 700 comprises a phase locked loop (PLL) 704, a counter 706 and a memory 708. The memory 708 stores a waveform or waveforms for the clock 702. The memory 708 may be a random access memory or a read only memory. The phase lock loop 704 provides a multiplied frequency to the counter 706, which generates a control signal for reading the memory 708 in response to the multiplied frequency.

In the foregoing description, various methods and apparatus, and specific embodiments are described. However, it should be obvious to one conversant in the art, various alternatives, modifications, and changes may be possible without departing from the spirit and the scope of the invention which is defined by the metes and bounds of the appended claims.

What is claimed is:

1. An electrical waveform generating circuit comprising:
   a power amplifier having a first input and having an output for providing an amplified signal in response to a signal applied to the first input;
   a charge storage capacitor attached to the first input of the power amplifier and to ground; and
   a current source circuit having an output coupled to the first input of the power amplifier for providing one of a selectable or programmable waveform in response to a control signal applied to an input of the current source circuit.

2. The electrical waveform generating circuit of claim 1 further comprising a transducer coupled to the output of the power amplifier.

3. The electrical waveform generating circuit of claim 1 wherein the selectable waveform on the output of the current-sources is selected from one of: approximately trapezoid, approximately triangle, piecewise-approximately linear or arbitrary.

4. The electrical waveform generating circuit of claim 1 wherein the output of the power amplifier is coupled to and driving one of a piezoelectric transducer or electrostatic array probe.

5. The electrical waveform generating circuit of claim 1, wherein the electrical waveform generating circuit is formed in an integrated circuit ultrasound transmit pulse generator IC for one of single channel or multiple channels ICs.

6. The electrical waveform generating circuit of claim 1, wherein the power amplifier is formed in a single integrated circuit ultrasound transmit pulse generator IC package and the capacitor and the current-source circuit are formed in multiple IC packages.

7. The electrical waveform generating circuit of claim 1, wherein the current source circuit provides an enable control signal to the power amplifier to enable the power amplifier.

8. The electrical waveform generating circuit of claim 1, wherein the power amplifier includes a complementary MOSFET source follower.

9. The electrical waveform generating circuit of claim 8, wherein the power amplifier provides the amplified signal in response to a bias voltage control.

10. The electrical waveform generating circuit of claim 1, wherein the power amplifier includes a complementary bipolar transistors emitter follower.

11. The electrical waveform generating circuit of claim 1, wherein the current source circuit comprises a pair of transistors arranged in a cascode configuration to one of sink or source current into the capacitor.

12. The electrical waveform generating circuit of claim 1, further comprising a current control circuit coupled to the current source circuit, the current control circuit providing a plurality of control signals to the current source circuit to control timing and current levels for current sourcing and sinking of the current source circuit, for turning the current source circuit on or off, or changing the sources current values.

13. The electrical waveform generating circuit of claim 12, wherein the current control circuit further comprises a level shift circuit to shift a low voltage logic level of an input control signal to a high voltage level.

14. The electrical waveform generating circuit of claim 12, wherein one terminal of the capacitor is selectively coupled to one of a fixed voltage source, regulated voltage source, zero volt node of common ground, an operational amplifier input end or virtual ground.

15. The electrical waveform generating circuit of claim 1, wherein the current source circuit comprises sourcing and sinking current sources that are a constant-current type.

16. The electrical waveform generating circuit of claim 1, wherein the current source circuit comprises sourcing and sinking current sources that are voltage-sources.

17. The electrical waveform generating circuit of claim 1, further comprising a switch coupling the input of the power amplifier and to a ground node.

18. The electrical waveform generating circuit of claim 17, wherein the switch comprises back-to-back MOSFETs.

19. The electrical waveform generating circuit of claim 1 further comprising a clock generator for providing a chirp clock to the current source, wherein the current source provides the selectable waveform in response to the chirp clock.

20. The waveform generator of claim 19, wherein the clock generator further comprises a memory for storing a waveform and generating chirp clock based on the waveform in one of synchronization or synthesized from the input frequency clock.

21. An electrical waveform generating circuit comprising:
a power amplifier having a first input and having an output for providing an amplified signal in response to a signal applied to the first input;
a transducer coupled to the output of the power amplifier;
a charge storage capacitor attached to the first input of the power amplifier and to ground;
a current source circuit having an output coupled to the first input of the power amplifier for providing one of a selectable or programmable waveform in response to a control signal applied to an input of the current source circuit;
a current control circuit coupled to the current source circuit, the current control circuit providing a plurality of control signals to the current source circuit to control timing and current levels for current sourcing and sinking of the current source circuit, for turning the current source circuit on or off, and changing the sources current values.

22. The electrical waveform generating circuit of claim 21 further comprising a cross-coupled diode circuit attached to the output of the power amplifier and to the transducer.

23. The electrical waveform generating circuit of claim 21, further comprising a switch coupling the input of the power amplifier and to ground.

24. The electrical waveform generating circuit of claim 23, wherein the switch comprises back-to-back MOSFETs.

25. The electrical waveform generating circuit of claim 21 further comprising a clock generator for providing a chirp clock to the current source, wherein the current source provides the selectable waveform in response to the chirp clock.

26. The waveform generator of claim 25, wherein the clock generator further comprises a memory for storing a waveform and generating chirp clock based on the waveform in one of synchronization or synthesized from the input frequency clock.

27. The electrical waveform generating circuit of claim 21, wherein the power amplifier includes a complementary MOSFET source follower.

28. The electrical waveform generating circuit of claim 21, wherein the power amplifier includes a complementary bipolar transistors emitter follower.

29. The electrical waveform generating circuit of claim 21, wherein the current source circuit comprises a pair of transistors arranged in a cascode configuration to one of sink or source current into the capacitor.

30. The electrical waveform generating circuit of claim 21, wherein the current control circuit further comprises a level shift circuit to shift a low voltage logic level of an input control signal to a high voltage level.

* * * * *